United States Patent [19]
Benson et al.

[11] Patent Number: 6,118,028
[45] Date of Patent: Sep. 12, 2000

[54] METHOD OF MAKING TRIFLUOROMETHOXYBENZENES

[75] Inventors: Kevin R. Benson, West Seneca; John Hickey, Grand Island; William S. Derwin, Grand Island; Michael J. Fifolt, Grand Island; Sanjay Mandal, Grand Island, all of N.Y.

[73] Assignee: Occidental Chemical Corporation, Dallas, Tex.

[21] Appl. No.: 09/039,919

[22] Filed: Mar. 16, 1998

[51] Int. Cl.⁷ .............................. C07C 41/14; C07C 41/22
[52] U.S. Cl. ............................................... 568/655
[58] Field of Search .................. 568/655, 579, 568/626, 630

[56] References Cited

U.S. PATENT DOCUMENTS 4,620,040  10/1986  Alsop ........................................ 568/656

FOREIGN PATENT DOCUMENTS 05000988  10/1993  Japan .
765527    1/1957   United Kingdom .

*Primary Examiner*—Rosalynd Keys
*Attorney, Agent, or Firm*—Anne E. Brookes; Richard D. Fuerle

[57] ABSTRACT

Disclosed is a process for making an α,α,α-trifluoromethoxybenzene by reacting an α,α,α-trichloromethoxybenzene or an α,α,α-tribromomethoxybenzene with gaseous hydrogen fluoride in the presence of a catalyst of antimony pentachloride, molybdenum pentachloride, molybdenum dichloride dioxide, molybdenum oxide, or a mixture thereof. The hydrogen fluoride is used in an amount of about 1 to about 1.4 times stoichiometric and is at about atmospheric pressure. The reaction is performed at about 30 to about 100° C.

21 Claims, No Drawings

METHOD OF MAKING TRIFLUOROMETHOXYBENZENES

BACKGROUND OF THE INVENTION

This invention relates to a method of making α,α,α,-trifluoromethoxybenzene by reacting an α,α,α,-trichloromethoxybenzene or an α,α,α,-tribromomethoxybenzene with hydrogen fluoride. In particular, it relates to performing this reaction using gaseous hydrogen fluoride at atmospheric pressure.

α,α,α,-Trifluoromethoxybenzene is an intermediate used in making agricultural chemicals. It has been made by a variety of different processes, including the reaction of hydrogen fluoride with α,α,α,-trichloromethoxybenzene. That reaction has been performed using liquid hydrofluoric acid at low temperatures and gaseous hydrofluoric acid at high temperatures and high pressures, with and without catalysts, usually with a large excess of hydrogen fluoride. The reaction is difficult to perform under these conditions because hydrogen fluoride is such a highly reactive and dangerous chemical. In addition to the safety problems, the yields are often low, and the product is frequently contaminated with byproducts and tar.

SUMMARY OF THE INVENTION

We have discovered that α,α,α,-trichloromethoxybenzenes and α,α,α,-tribromomethoxybenzenes can be reacted with gaseous hydrogen fluoride at atmospheric pressure using an antimony or molybdenum catalyst, without a large excess of hydrogen fluoride. Performing the reaction under these conditions is much safer due to the low pressures, moderate temperatures, and much lower concentrations of the hydrogen fluoride. Amazingly, although our invention does not employ the extreme conditions used in the prior art, we are nevertheless able to achieve higher yields of the α,α,α,-trifluoromethoxybenzene product than the yields reported in most of the prior art and with little or no contamination of the product with byproducts and tar.

DESCRIPTION OF THE PREFERRED EMBODIMENTS

Substrates useful in the process of this invention are typically liquids having the general formula:

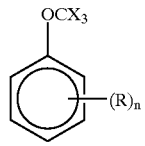

where X is chlorine or bromine, R is X', $NO_2$, COX', CN, or $CF_3$, X' is halogen, and n is 0 to 3. Preferably, n is 0 and X is chlorine because trifluoromethoxybenzene is commercially the most important product and the substrate α,α,α,-trichloromethoxybenzene is less expensive than α,α,α,-tribromomethoxybenzene. If n is 1, R is preferably in the para position as the products made from those substrates are more important. A second preferred substrate is parachloro-α,α,α,-trichloromethoxybenzene because the product, parachloro-α,α,α,-trifluoromethoxybenzene, has some commercial applications.

The catalysts used in this invention are antimony pentachloride, $SbCl_5$, molybdenum pentachloride, $MoCl_5$, molybdenum dichloride dioxide, $MoO_2Cl_2$, molybdenum oxide, $MoO_3$, or a mixture thereof. The preferred catalyst is antimony pentachloride as less hydrogen fluoride is required with that catalyst. Other catalysts that were tried, such as $TaCl_5$, were not successful. The amount of catalyst used should be about 0.2 to about 1.5 wt %, based on the weight of the substrate. Less catalyst will result in a slow reaction and the substrate may not be completely fluorinated. More catalyst is unnecessary, wasteful, and may contaminate the product. Preferably, the amount of antimony pentachloride used is about 0.5 to about 1 wt %, based on the weight of the substrate. Antimony pentachloride is a liquid and the other catalysts are solids.

The hydrogen fluoride must be in a gaseous state at a temperature between about 30 and about 100° C. Lower temperature may result in incomplete fluorination of the substrate and at higher temperatures more tar and byproducts are produced. A preferred temperature range is about 30 to about 70° C. It is not necessary to use pressures higher than atmospheric pressure of the hydrogen fluoride in order to obtain the benefits of this invention, although slightly higher pressures will not significantly reduce the yield. The amount of hydrogen fluoride used should be about 1 to about 1.4 times the amount stoichiometrically required. Less hydrogen fluoride will, of course, result in unreacted substrate and more is a waste of hydrogen fluoride. It is preferable to use about 1 to about 1.2 times the amount of hydrogen fluoride that is stoichiometrically required.

A typical procedure for performing the reaction is to charge the reactor with the substrate and the catalyst, close the reactor, heat it to the desired temperature, and add the hydrogen fluoride, but other procedures can also be used. We have discovered that if all the catalyst is added initially it is usually necessary to add additional catalyst later to make the reaction go to completion. The use of additional catalyst can be avoided by adding the catalyst in two or more portions as the reaction proceeds or by metering in the catalyst along with the hydrogen fluoride. Metering in is easily accomplished and is the preferred procedure.

The following examples further illustrate this invention.

EXAMPLE 1

Into a 500 mL polytetrafluoroethylene reactor equipped with a magnetic stirring bar, a condenser, a thermocouple, and an inlet for HF, was placed 350 g (1.66 mol) of pure α,α,α,-trichloromethoxybenzene. The reactor was heated to 40° C. After introducing 3.5 g (1 wt % of the starting material) antimony pentachloride, HF gas was added to the solution at a rate of 800 mL/min for three hours, for a total of 128 g (6.4 mole) HF. While the reaction temperature was maintained between 40 and 45° C., the condenser was cooled to −25° C. using a chiller. When the reaction was complete, the temperature of the mixture dropped quickly and both the HF gas flow and the heat were turned off. Nitrogen gas was purged through the reactor until all of the HF had been removed. The reactor was opened to purify and isolate the product. An assay of the reaction mixture by gas chromatography (GC) showed 99% of the desired α,α,α-trifluoromethoxybenzene.

The reaction mixture was run through a soda ash column, yielding a light yellow product that was distilled to obtain 100% pure α,α,α-trifluoromethoxybenzene in 88 wt % isolated yield.

EXAMPLE 2

When Example 1 was repeated, except with an initial catalyst charge of 0.27 wt %, the reaction proceeded smoothly to 60% α,α,α-trifluoromethoxybenzene. At this time another 0.28 wt % catalyst was added to complete the reaction, as the HF efficiency was decreasing. This was noted by a decrease in the temperature of the reaction mixture. The amount of HF used in this example was about 1.16 times the amount stoichiometrically required and the overall HF efficiency in this example was higher than in Example 1. An assay of the final reaction mixture by GC showed 99% of the desired α,α,α-trifluoromethoxybenzene.

EXAMPLE 3

Knowing that a total of 0.55 wt % (in two steps) catalyst was required in Example 2, Example 1 was repeated with an initial charge of 0.53 wt % catalyst. The reaction proceeded smoothly to 55% α,α,α-trifluoromethoxybenzene. At this time another 0.29 wt % catalyst was added to complete the reaction, as the HF efficiency was decreasing. This was noted by a decrease in the temperature of the reaction mixture. The amount of HF used in this example was about 1.035 times the amount stoichiometrically required, which yielded the best overall HF efficiency. An assay of the final reaction mixture by GC showed 99% of the desired α,α,α-trifluoromethoxybenzene.

EXAMPLE 4

Example 1 was repeated, except that the initial charge of the catalyst was 0.29 wt % and the reaction temperature was maintained between 70 and 75° C. The reaction yielded 30% α,α,α-trifluoromethoxybenzene after 2 hours. Since the HF efficiency was decreasing, two additional charges, 0.46 and 0.21 wt %, of the catalyst were required to complete the reaction. The amount of HF used in this example was very close to the amount used in Example 1. An assay of the final reaction mixture by GC showed 99% of the desired α,α,α-trifluoromethoxybenzene.

EXAMPLE 5

(Comparative)

Example 1 was repeated except that the initial charge of the catalyst was 0.28 wt % and the reaction temperature was maintained between 8.5 and 12.8° C. The reaction yielded only 45% α-chloro-α,α-difluoromethoxybenzene and no α,α,α-trifluoromethoxybenzene after approximately ⅔ of the stoichiometric amount of HF had been introduced. The reaction was aborted.

EXAMPLE 6

Example 1 was repeated except that the catalyst was $MoO_2Cl_2$ with an initial charge of 1.29 wt % and the reaction temperature was maintained between 35 and 45° C. The reaction yielded 90% α-chloro-α,α-difluoromethoxybenzene and 8% α,α,α-trifluoromethoxybenzene after approximately 85% of the stoichiometric amount of HF had been introduced. At this time another 0.23 wt % catalyst was added to the reactor, as the HF efficiency was decreasing, as indicated by a drop in reaction temperature. When 1.7 times the stoichiometric amount of HF required was introduced, the reaction mixture showed 9% α-chloro-α,α-difluoromethoxybenzene and 90% α,α,α-trifluoromethoxybenzene. Similar results were obtained with $MoCl_5$ as a catalyst.

EXAMPLE 7

(Comparative)

Example 1 was repeated except that the catalyst was $TaCl_5$ with an initial charge of 1.4 wt % and the reaction temperature was maintained between 70 and 90° C. The reaction yielded 97% α-chloro-α,α-difluoromethoxybenzene and only 1% α,α,α-trifluoromethoxybenzene after approximately 70% of the stoichiometric amount of HF had been introduced. At this time another 1.4 wt % catalyst was added to the reactor, as the HF efficiency was decreasing (reaction temperature fell). When 100% of the stoichiometric amount of HF had been introduced, the reaction mixture showed 67% α-chloro-α,α-difluoromethoxybenzene and 29% α,α,α-trifluoromethoxybenzene. The reaction was aborted.

EXAMPLE 8

Example 1 was repeated except that 1.3 wt % $MoO_3$ catalyst was used and the reaction temperature was maintained between 30 and 50° C. The reaction yielded 36% α-chloro-α,α-difluoromethoxybenzene and 56% α,α,α-trifluoromethoxybenzene after approximately 1.35 times the stoichiometric amount of HF required had been introduced. The reaction was aborted.

We claim:

1. A method of making a α,α,α-trifluoromethoxybenzene comprising reacting a substrate having the general formula:

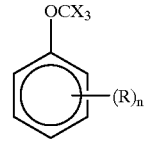

with about 1 to about 1.4 times the stoichiometric amount of hydrogen fluoride at approximately atmospheric pressure and at a temperature between about 30 and about 100° C. in the presence of about 0.2 to about 1.5 wt %, based on the weight of said substrate, of a catalyst selected from the group consisting of antimony pentachloride, molybdenum pentachloride, molybdenum dichloride dioxide, molybdenum oxide, and mixtures thereof, where X is chlorine or bromine, R is X', $NO_2$, COX', CN, or $CF_3$, X' is halogen, and n is 0 to 3.

2. A method according to claim 1 wherein n is 0.

3. A method according to claim 1 wherein X is chlorine.

4. A method according to claim 1 wherein said substrate is α,α,α-trichloromethoxybenzene.

5. A method according to claim 1 wherein said substrate is parachloro-α,α,α-trichloromethoxybenzene.

6. A method according to claim 1 where n is 1 and R is in the para position.

7. A method according to claim 1 wherein n is 1 and R is chlorine.

8. A method according to claim 1 wherein said catalyst is antimony pentachloride.

9. A method according to claim 1 wherein the temperature of said hydrogen fluoride is about 30 to about 70° C.

10. A method according to claim 1 wherein the amount of said hydrogen fluoride is about 1 to about 1.2 times stoichiometric.

11. A method according to claim 1 wherein the amount of said antimony pentachloride is about 0.5 to about 1 wt %, based on the weight of said substrate.

12. A method according to claim 1 wherein a reactor is charged with said substrate, said catalyst is added to said reactor, said reactor is closed and heated, and said hydrogen fluoride is added to said reactor.

13. A method according to claim 1 wherein said catalyst is metered in to said reactor with said hydrogen fluoride.

14. A method according to claim 1 wherein said catalyst is added in at least two portions to said reactor.

15. A method of making an α,α,α-trifluoromethoxybenzene comprising (1) charging a reactor with a substrate having the general formula:

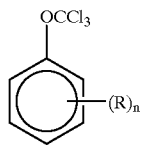

where R is X', NO$_2$, COX', CN, or CF$_3$, X$^3$ is halogen, and n is 0 to 3;

(2) adding to said reactor about 0.5 to about 1 wt %, based on the weight of said substrate of a catalyst of antimony pentachloride;
(3) closing said reactor;
(4) heating said reactor to a temperature of about 30 to about 70° C.; and
(5) adding to said reactor about 1 to about 1.2 times stoichiometric of gaseous hydrogen fluoride.

16. A method according to claim 15 wherein said substrate is α,α,α-trichloromethoxybenzene.

17. A method according to claim 15 wherein said substrate is parachloro-α,α,α-trichloromethoxybenzene.

18. A method according to claim 15 wherein R is chlorine.

19. A method according to claim 15 wherein said catalyst is metered in to said reactor with said hydrogen fluoride.

20. A method according to claim 15 wherein said catalyst is added to said reactor in at least two portions.

21. A method of making α,α,α-trifluoromethoxybenzene comprising charging a reactor with α,α,α-trichloromethoxybenzene, closing said reactor, heating said reactor to about 30 to about 70° C., and metering into said reactor (1) about 0.5 to about 1 wt %, based on the weight of said α,α,α-trichloromethoxybenzene, of antimony pentachloride; and
(2) about 1 to about 1.2 times stoichiometric of gaseous hydrogen fluoride at about atmospheric pressure.

\* \* \* \* \*